(12) United States Patent
Sakurada et al.

(10) Patent No.: US 9,144,237 B2
(45) Date of Patent: Sep. 29, 2015

(54) STERILIZING AND DEODORIZING AGENTS, THEIR METHOD OF MANUFACTURE AND USES

(75) Inventors: Tsukasa Sakurada, Kiso-gun (JP); Charles P. Gerba, Tucson, AZ (US)

(73) Assignee: Tsukasa Sakurada, Nagano-Ken (JP)

( * ) Notice: Subject to any disclaimer, the term of this patent is extended or adjusted under 35 U.S.C. 154(b) by 194 days.

(21) Appl. No.: 13/572,437

(22) Filed: Aug. 10, 2012

(65) Prior Publication Data

US 2014/0044801 A1 Feb. 13, 2014

(51) Int. Cl.
*A01N 25/08* (2006.01)
*A01N 59/16* (2006.01)
*C09D 5/14* (2006.01)

(52) U.S. Cl.
CPC ............... *A01N 25/08* (2013.01); *A01N 59/16* (2013.01); *C09D 5/14* (2013.01); *Y10T 156/10* (2015.01); *Y10T 442/2525* (2015.04)

(58) Field of Classification Search
None
See application file for complete search history.

(56) References Cited

U.S. PATENT DOCUMENTS

| | | | |
|---|---|---|---|
| 4,851,163 A * | 7/1989 | Stanton et al. | 261/122.1 |
| 5,151,122 A * | 9/1992 | Atsumi et al. | 106/35 |
| 2005/0245627 A1 * | 11/2005 | Takashima | 521/99 |

FOREIGN PATENT DOCUMENTS

| | | | |
|---|---|---|---|
| JP | 2963657 | | 10/1999 |
| JP | 3040724 | | 5/2000 |
| JP | 3265355 | | 3/2002 |
| JP | 3368338 | | 1/2003 |
| JP | 4189074 | | 12/2008 |
| JP | 2009-066594 A | | 4/2009 |
| JP | 4542601 | | 9/2010 |
| KR | 2005022043 A | * | 3/2005 |
| KR | 20050022043 A | * | 3/2005 |

* cited by examiner

*Primary Examiner* — Carlos Azpuru
*Assistant Examiner* — Casey Hagopian
(74) *Attorney, Agent, or Firm* — DLA Piper LLP (US)

(57) ABSTRACT

The sterilizing and deodorizing agents target bacteria, odors, toxic substances, etc. and are made from silver as metal particles and titanium dioxide as ceramic particles by (1) thermal bonding or (2) pressure bonding or (3) thermal/pressure bonding and mixing the resultant with hydroxyapatite as an adsorptive material. The agent can be mixed with ink, bonding agents and paints and applied to a variety of substrates.

28 Claims, 11 Drawing Sheets

US 9,144,237 B2

STERILIZING AND DEODORIZING AGENTS, THEIR METHOD OF MANUFACTURE AND USES

BACKGROUND OF THE INVENTION

1. Field of the Invention

The present invention pertains to agents that are designed to continuously exert excellent sterilizing and deodorant effects, etc. for a long period of time through being adhered to the surfaces of the substrates such as paper, textiles, plastics, metals, ceramics and compound products.

2. Prior Art

In the prior art there exists sterilizing and deodorizing agents. However, these agents are either of a solid or liquid form. The solid agents are related technologies, but utilize the oxidation-reduction ability of a photocatalyst. While the photocatalyst can function over long periods of time, they can only function in the presence of UV light and do not function in the dark. The liquid agents, such as alcohol and chlorine agents, do not normally require light, but only function for short periods of time and either evaporate and/or deteriorate quickly. Still further, generally many of the liquid sterilizing agents are toxic and therefore have the disadvantage of burdening the environment.

While these photocatalysts have sterilizing and deodorizing effects wherein bacteria, viruses, allergens, and various odor causing organic materials are decomposed by radicals, they are produced through the oxidation-reduction reaction occurring on the surfaces of photocatalysts or photocatalysts in the presence of UV light. However, because the oxidation-reduction reaction only occurs at the interface of photocatalysts and the reaction is very weak under the visible light, photocatalysts are regarded as problematic in that they are not useful in dark environments.

To make these photocatalysts useful, attempts, such as increasing the content of photocatalysts or selecting the right crystal structure, have been made to solve the above problem. However, the aforementioned decomposition utilizing the oxidation-reduction reaction does not have the ability to choose what to decompose or what not to decompose; in other words, all organic materials that exist close to the photocatalyst are decomposed. Consequently, photocatalysts have another problem in that a substrate with photocatalysts and an organic material with photocatalysts crumble when the oxidation-reduction reaction is too strong.

In addition, the prior art agents also have the disadvantage of burdening the environment.

SUMMARY OF THE INVENTION

Accordingly, it is an object of the present invention to overcome the problems of the prior art described above.

It is a particular object of the present invention to provide an agent which does not require light to function and persists for long periods of time.

It is yet another object of the present invention to provide an agent with superior sterilizing effect to metal compounds that exist in the prior art.

It is yet another object of the present invention to provide an agent which is useful with a plurality of substrates and carriers.

It is still another object of the present invention to provide an agent which is easy and inexpensive to manufacture and use.

The above mention features and objects of the present invention are accomplished by a combination of a ceramic having a metal using (1) thermal bonding, (2) pressure bonding or (3) thermal/pressure bonding bonded thereto. The ceramic is in a particle form and is selected from the group consisting of $TiO_2$, $Cr_2O_3$, $Co_3O_4$, $Al_2O_3$, SiC, CdS, CdSe, $WO_3$, $Fe_2O_3$, $SrTiO_2$, or $KNbO_3$ and mixtures thereof, preferably Titanium dioxide, and the metal is in a particle form and is selected from the group consisting of gold, silver, platinum, or copper powder or any combination thereof, preferably silver.

The metal is bonded to the ceramic using thermal bonding, pressure bonding and thermal/pressure bonding.

The completed agent can be mixed with paint, inks, adhesive, gels, layer forming agents and/or by itself and printed, painted, sprayed and inserted into or intertwined on or with a variety of different substrates such as paper, textiles, plastics, metals, ceramics and compound products. Also, the agent can be mixed with a variety of carriers such as lotions, creams, gels, ointments, water and other liquids or semi-liquids which can be applied to the human body and/or other surfaces.

The agents of the present invention do not become effective through becoming dissolved from the substrate into water. Instead, the agent of the present invention becomes effective through remaining on the substrate to keep decomposing organic matter, and consequently the effectiveness lasts a long time and has no adverse effects on the environment.

DETAILED DESCRIPTION OF THE INVENTION

The present invention comprises a metal that is thermal bonded, pressure bonded, thermal/pressure bonded to a ceramic. The ceramic is selected from $TiO_2$, $Cr_2O_3$, $Co_3O_4$, $Al_2O_3$, SiC, CdS, CdSe, $WO_3$, $Fe_2O_3$, $SrTiO_3$, $KNbO_3$, etc., but preferably $TiO_2$ since it is chemically stable, approved as a food additive, unassociated with health problems, and easily available and inexpensive. In order to assure a larger surface area and good adherence workability, the particle size of the ceramic is 0.3 to 100 μm and is preferred to be 0.3 to 50 μm.

The metal used in the presently-invented agents constitutes, a metal selected from: gold, silver, platinum, copper, combinations thereof and other various metal particles, preferably silver. From an economic standpoint, however, a combination of $TiO_2$ and silver is preferred because it has the aforementioned characteristics and is non-toxic and therefore is safe and does not influence the ecological system. In view of the relationship between the metal and the ceramic, the particle size of the metal is preferred to be 0.3 to 50 µm. In order for the agent to be effective in sterilizing bacteria, eliminating odors, etc, the weight ratio of the ceramic to the metal is preferred to be 100:0.01-30, and 100:0.05-15 in particular. The size of the agent comprising the metal bonded to the ceramic is from 0.3 to 100 µm. The present agent can also be produced mixing the ceramic with the metal bonded thereto with adsorptive materials.

Adsorptive material such as zeolite, sepiolite, apatite, activated carbon, etc. can also be used in the presently invented agent for adsorbing and retaining not only bacteria, viruses, allergens, fungi but also other target objects such as offensive odor substances and toxic substances, etc. The present invention particularly uses Hydroxyapatite which functions as the adsorptive material. The particle size of the Hydroxyapatite of the present invention is preferred to be 0.3 to 50 µm in particular, for ensuring larger surface areas and for achieving a good workability. The weight ratio of the mixture of the ceramic with the metal bonded thereto and the Hydroxyapatite (i.e. the adsorptive material) is preferred to be 100:1-50, and 100:1-30 in particular, for desired effects of sterilization, deodorization, etc.

The present agent can be produced through mixing the ceramic with the metal bonded thereto with the Hydroxyapatite, i.e. the adsorptive material.

Figure 1:
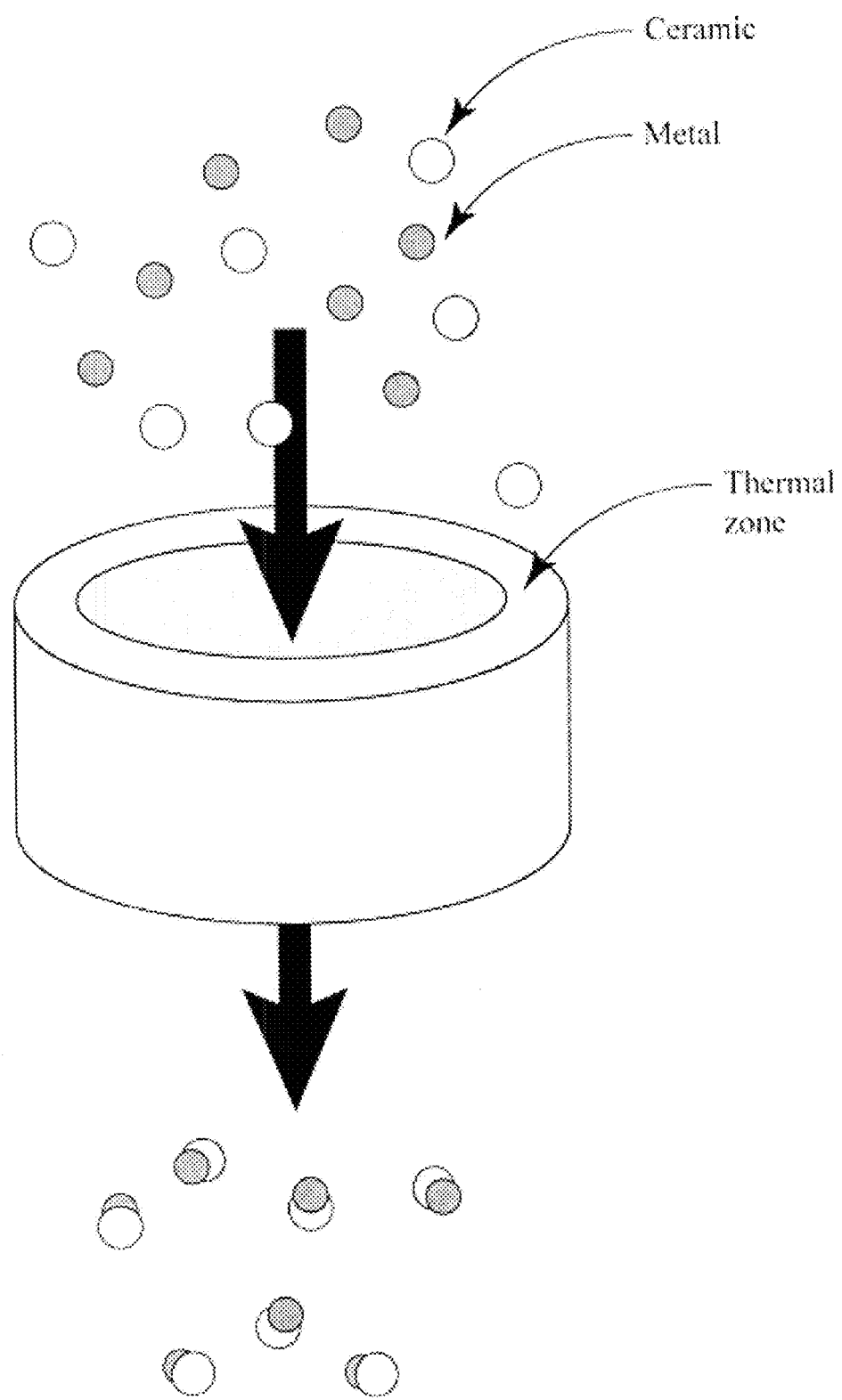
FIG. 1 shows the manner of how ceramic is thermally bonded with metal according to the present invention.
Figure 2:
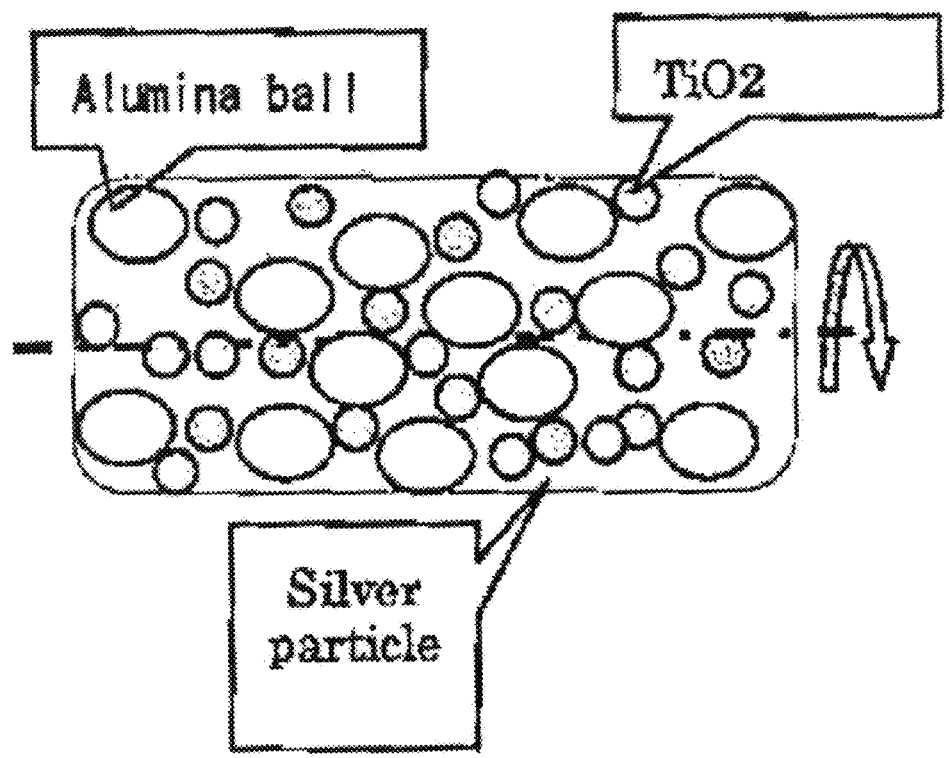
FIG. 2 shows the manner of how ceramic is pressure bonded to metal according to the present invention.
Figure 3:
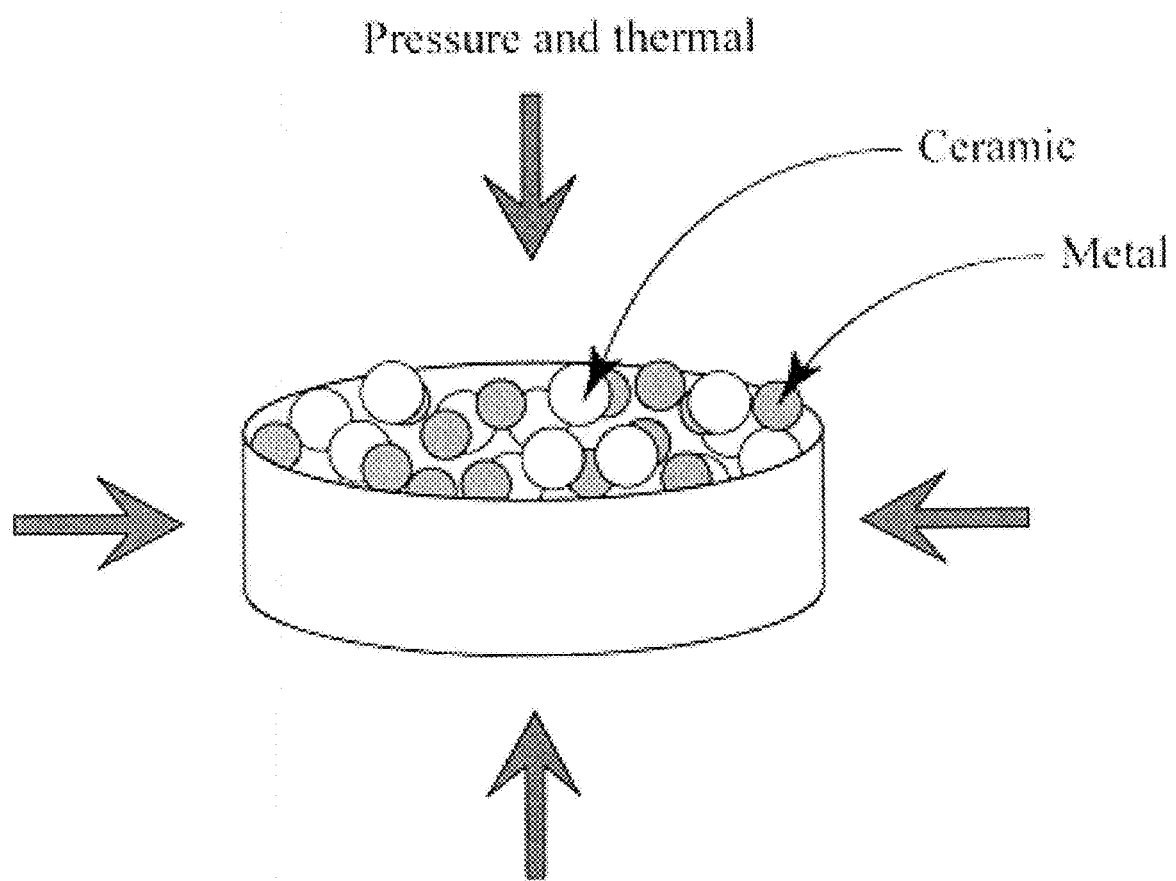
FIG. 3 shows the manner of application of pressure and heat to ceramic and metal for bonding according to the present invention.

The ceramic with the metal bonded thereto can be manufactured using (1) thermal bonding of FIG. 1, (2) pressure bonding of FIG. 2 or (3) thermal/pressure bonding as shown in FIG. 3.

Figure 4:
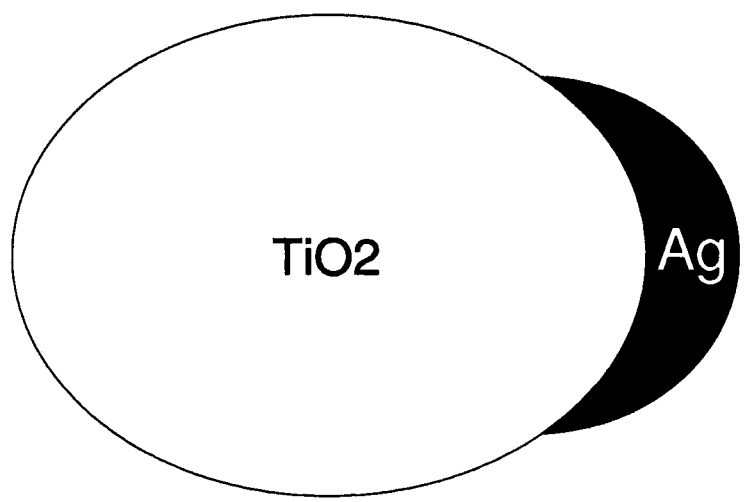
FIG. 4 shows titanium dioxide with silver thermal/pressure bonded thereto.
Figure 5:
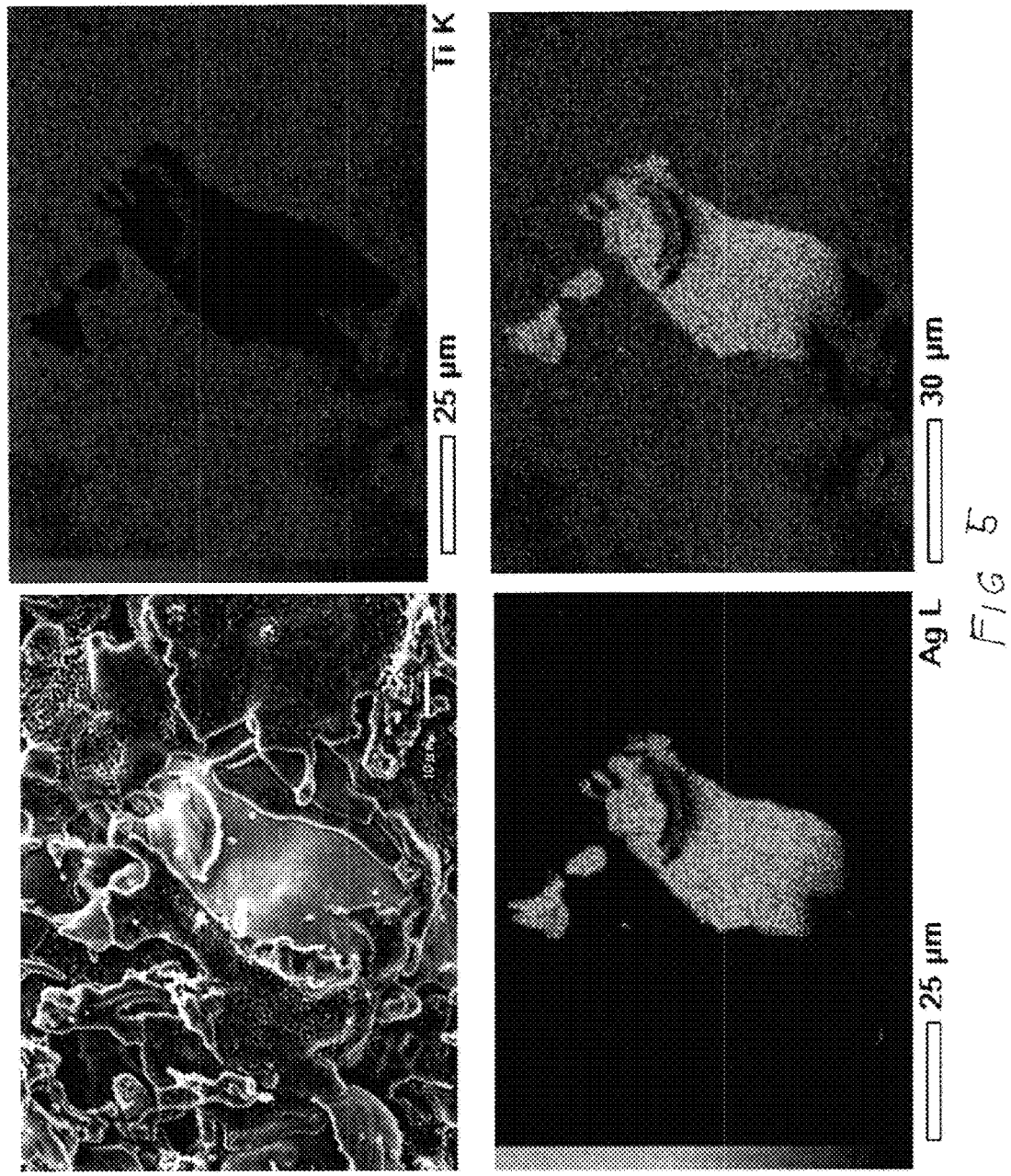
FIG. 5 shows SEM images that describe the turning of titanium dioxide and silver into a film form as mapping images.

In this process the ceramic ($TiO_2$) and metal (silver) particles are bonded through a high temperature zone as shown in FIG. 1. In the process, a part of the metal is ingrown into particles of the ceramic. The instantaneous temperature of the hot temperature zone is about substantially 2900 degrees Celsius. In this process the ceramic and metal are bonded through the use of a ball mill, as shown in FIG. 2. The ball mill contains very hard balls made of materials such as Alumina or Zirconium and are approximately 0.1 mm and 0.004 mg. Furthermore, as shown in FIG. 3, the ceramic and the metal particles are can be bonded by simultaneously applying heat and pressure. The silver is 80 to 99.9% pure and the Titanium Dioxide is about 90 to 99% pure. The resultant ceramic, titanium dioxide with silver thermal/pressure bonded thereto will be as substantially shown in FIG. 4, and FIG. 5 shows SEM (scanning electron microscope) images that describe the turning of titanium dioxide and silver into a film form as mapping images.

While the above process to bond the metal to the ceramic is described above, other processes could be used such as high temperature rollers and high temperature ultrasonic bonding.

The agent of the present invention can be adhered to target objects such as wood, cloth, plastic, metal, ceramic, concrete, etc. through coating, etc. to be used, and they can also be used as an inside filler material as well. While the agent of the present invention are useful as they are, they can also become useful materials through being dispersed in dispersing agents, such as water, organic solvents, adhesives, etc. The agents of the present invention can be adhered to the target objects through coating, etc. to be used, and they can be contained as an inside filler material as well.

Besides the above forms, the present invention can take the form of printing ink and paint materials. These forms also aim to provide sterilization and deodorizing and decorative effects. Printing ink, another form of the present invention, not only contains the ceramic with the metal bonded thereto, and the Hydroxyapatite as an adsorptive material but also contains at least color materials and carriers. Printing ink contains other ingredients as well if necessary. As color materials, not only inorganic pigments and organic pigments (i.e. color materials commonly used for printing ink) but also dyes such as solvent dye and disperse dye, etc. can be listed as examples. As carriers, the following can be listed:

oil, for instance, drying oil such as linseed oil, etc., semi-drying oil such as soybean oil, etc., and nondrying oil such as caster oil, etc.: resins, for instance, natural resin (such as rosin, modified rosin, gilsonite, etc.), natural resin derivative, phenol resin, alkyd resin, xylene resin, urea resin, melamine resin, polyamide resin, acrylic resin, epoxy resin, ketone resin, petroleum resin, polyvinyl chloride resin, polyvinyl acetate, urethane resin, chlorinated polypropylene, chlorinated rubber, cyclized rubber, cellulosic derivative, and reactive resin; and plasticizer.

Also, as other materials, the following can be listed:

wax components in natural wax and synthetic wax, dryer, dispersing agent, wetting agent, cross-linking agent, gelling agent, thickening agent, anti-skinning agent, stabilizer, flattening agent, defoamer, anti-flooding agent, and anti-fungus agent, etc.

While there is no specific mixture ratio for these components, the mixture ratio found in the common printing ink on the market is useful.

In order for printing ink to exert the effects of sterilizing bacteria and eliminating odors, etc. and ensure a proper printability, the preferred total amount of the agent of the present invention comprising a ceramic with a metal pressure bonded thereto is 3-80% of the total weight of the printing ink, and 10-80% in particular.

The forms or kinds of the printing ink are not particularly limited. They can be paste ink, solvent ink, or solvent-free ink. They can also be used as offset printing ink, lithographic printing ink, photogravure ink, screen process printing ink, intaglio printing ink, or special printing ink. In order to best achieve the purpose of the present invention, screen process printing ink, for example, screen process ink for paper, screen process ink for plastic, screen process ink for glass, screen process ink for metals and screen process ink for cloth, etc., are preferred among the aforementioned types.

In addition to the above, other forms of the present invention are explained below. Paint materials can not only contain the agent of the present invention comprising the ceramic particles with the metal bonded thereto but also contain at least film forming components and dispersing agents. Other components can be contained as well if necessary.

As film forming components, the following can be listed: synthetic resins such as cellulosic derivatives, phthalate resin, phenol resin, alkyd resin, amino alkyd resin, acrylic resin, epoxy resin, urethane resin, polyvinyl chloride resin, silicone resin, fluorocarbon resin, emulsion, water-soluble resin, etc.; and vegetable drying oil.

As dispersing agents, the following can be listed: petroleum solvent, aromatic solvent, alcohol solvent, ester solvent, ketone solvent, cellosolve solvent, water, etc. Moreover, in case of powder paint, solvents as dispersing agents are not necessary.

As other components, the following can be listed: pigments, for instance, inorganic pigments, such as titanium dioxide, lead chromate, Indian red, chrome oxide, carbon black, etc. organic pigments, such as Hansa yellow, novapermmm orange, quinacridone violet, copper phthaloeyanine, etc.; body pigments, such as precipitated calcium carbonate, barium sulfate, talc, clay, white carbon, etc.; special functional pigments represented by anti-corrosive pigments, such as zinc chromate, strontium chromate, zinc phosphate, aluminum phosphate, etc.

Furthermore, other than the above, the following can be incorporated as supplementary materials: dryer and polymerization catalyst for accelerating drying paint films; wetting agent, pigment dispersion agent, anti-flooding agent, and anti-setting agent for improving dispersibility of pigments! thickening agent, thixotropic agent, anti-sagging agent for regulating fluidity of pigments; and leveling agent, anti-foaming agent, anti-crawling agent, anti-floating agent as well as plasticizer, anti-skinning agent, electrostatic coating adjuvant, anti-scratch agent, anti-blocking agent, anti-UV agent, antifouling agent, antiseptic agent, anti-fungus agent, etc. for regulating painted surfaces. There is no special compounding ratio for these components, and the ratio should be apparent to one of ordinary skill in the art.

The compounding ratio found in the common painting materials on the market is useful. In order for the paint material to exert effects of sterilizing bacteria and eliminating odors, etc. and to ensure a proper paintability, the preferred total amount of the agent of the present invention comprising particles of ceramic with metal bonded thereto is a 3-80% of the total weight of the paint material, and 10-80% in particular.

The coating methods for the paint materials are not particularly limited. Methods, such as paintbrush coating, air spray coating, airless spray coating, electrostatic spray coating, powder coating, electro-deposition coating, curtain flow coating, roller-brush coating, etc. can be used.

The area needed for the presently-invented agents is not particularly limited. It depends according to the use of the agents.

The agent of the present invention can be used by mixing with liquid solution or agent that can be used to the human body and/or other surfaces representing the form of such as ointment, skin lotion, etc., and becomes effective for sterilizing bacteria and eliminating odors, etc. For example, mixing with liquid solution or agent is useful for a variety of products such as cosmetics, hand cream 11 in FIG. 6, ointment, ointment for medical treatment (for diseases that are associated with skin, epidermis such as tinea pedis, burn (scald), bedsore (decubitus), secondary disease of atopic dermatitis, wounds, etc.

And, the agent of the present invention can be used not only by mixing with liquid solution or agent but also by mixing with products such as resin, ceramics, adhesive, etc. and mixing with raw materials that are aimed for making materials.

Figure 7:
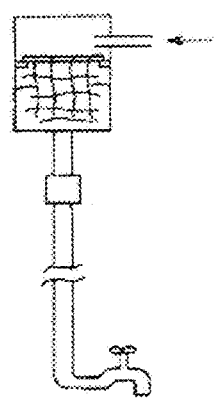
FIG. 7 shows a manner of agents of the present invention used for drinking water.
Figure 8:
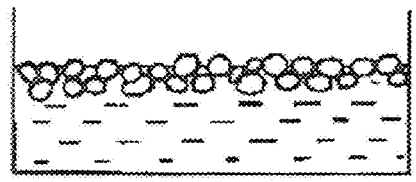
FIG. 8 shows a manner of agents of the present invention used for preservation for drinking water.
Figure 9:
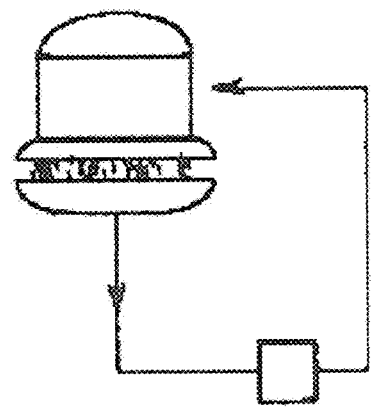
FIG. 9 shows a manner of agents of the present invention used for preservation for cooling tower.
Figure 10:
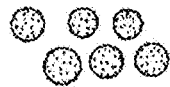
FIG. 10 shows a manner of agents of the present invention used for soil amendment.

As represented by the forms of printing ink, paint materials, etc., the presently-invented agents can be adhered in various forms to paper, wood, cloth, plastic, metal, concrete, etc. and become effective for sterilizing bacteria and eliminating odors, etc. Also, the agents of the present invention can exert decorative effects by being printed in desired patterns or graphics and can be used for a variety of decorations and other purposes for which light irradiation is considered unavailable. For example, being adhered to ceramics, metal, compound products, the agents of the present invention are useful for a variety of products such as drinking, water (FIG. 7), preservation for drinking water 12 in FIG. 6, storage of rainwater (FIG. 8), re-use of rainwater, reservoir, pond, washing and cleaning of vegetables, aquaculture (hydroponic culture), cooling tower (FIG. 9), bathtub, hot spring, soil amendment (FIG. 10), preservation for foodstuffs, freshness-keeping of food materials, drain ditch, tile 13 in FIG. 6, humidifier 14 in FIG. 6, medical equipment, filler of column, etc. and being adhered to paper, the presently invented agents are useful as housing materials, such as various wrapping paper, bags, etc. for preserving food, filters, medical materials, medical products, and materials, products as housing materials such as wall paper 15 in FIG. 6, shoji paper, fusuma paper, outer surface materials of furniture 16 in FIG. 6, etc. Additionally, by being adhered to resin, the agents of the present invention are useful for various kind of films such as decorative film, protective film, wrapping film of foodstuffs, for resin products for medical field such as catheter, endoscope, balloon, button of instrument, for products such as personal computers 30 in FIG. 6, telephone 17 in FIG. 6, jet-towels 18 in FIG. 6, play equipment, etc., for housing materials such as handrails 19 in FIG. 6, ceiling materials in FIG. 6, etc. as well as for materials needed for manufacturing those products. They are also useful as sizing agents that are contained in the raw materials of paper, woven and/or non-woven.

Figure 6:
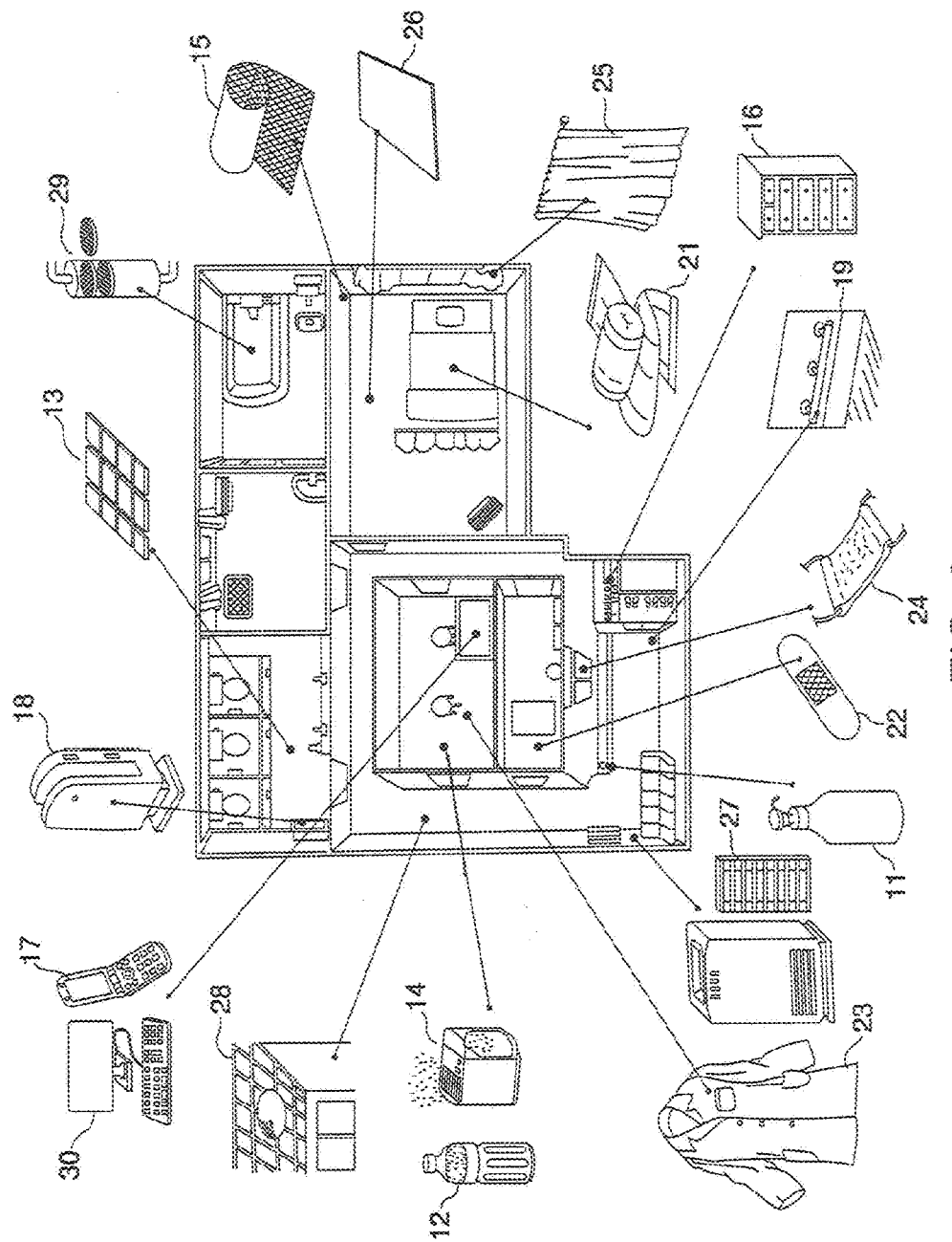
FIG. 6 illustrates use of agent according to the present invention for a variety of products.

By being adhered to cloth (textile materials) and woolen cloth, the presently invented agents are useful for various products such as cloths 21 in FIG. 6, materials for foodstuffs, materials for agriculture use, materials for medical use, adhesive plasters (adhesive bandages) 22 FIG. 6, gauze, bandages such as white bandages, gowns 23 in FIG. 6, uniforms, face masks 24 in FIG. 6, curtains 25 in FIG. 6, bedclothes (sheets), futon covers, blanket covers, pillow cases, etc., various covers (seat covers, floor cushion covers, etc.), table clothes, carpets 26 in FIG. 6, towels, handkerchiefs, etc. as well as for materials needed for manufacturing those products. They can also be used as materials for air-purification filters 27 in FIG. 6, water-purification filters 29 in FIG. 6, etc. Furthermore, they can be used for painting buildings and other structures, painting various products, and adding soil-resistant paint to ships, bridges, piers, etc. to repel aquatic animal such as acorn barnacle, Serpula, Mytilus, etc. They can be used for disallowing algae to start.

The presently-invented agents, first of all, adsorb bacteria, viruses, fungi, as well as bad odor substances, toxic substances, etc. Following their adsorption or at the same time as their adsorption, the bacteria and viruses, fungi, etc. are decomposed. Furthermore, the effect of the present invention stops the growth of or repels whatever is not decomposed. Also, without light irradiation the presently-invented agents have the same effects as they have under light irradiation in the normal temperature for human beings living on the Earth. Moreover, because proteins constituting bacteria, viruses, fungi, etc. are decomposed and disappear, the aforementioned effects do not diminish with time but last semi-permanently.

Bacteria, fungi, etc. favor the condition of high-temperature and high-humidity to multiply. The agent of the present invention is effective particularly under the condition of high-temperature and high-humidity and therefore is effective against bacteria and fungi.

Therefore, because the sterilizer components in the presently-invented agents are non-dissolvable, the agents represent a very widely useful technology to kill and suppress the growth of undesirable living organisms such as bacteria, fungi, etc. In places for where public hygiene, bacteria control, odor control, etc, are required such as houses, hospitals, nursing homes, public institutes, food factories, water plants, etc., since it is difficult to handle with one product, for products the agents of the present invention are used are extremely effective for using as "system" by combining them freely upon requests, and become effective for sterilizing bacteria and eliminating odors, etc. For example, a "system" that is aimed for infection control is shown in FIG. 6.

Figure 11:
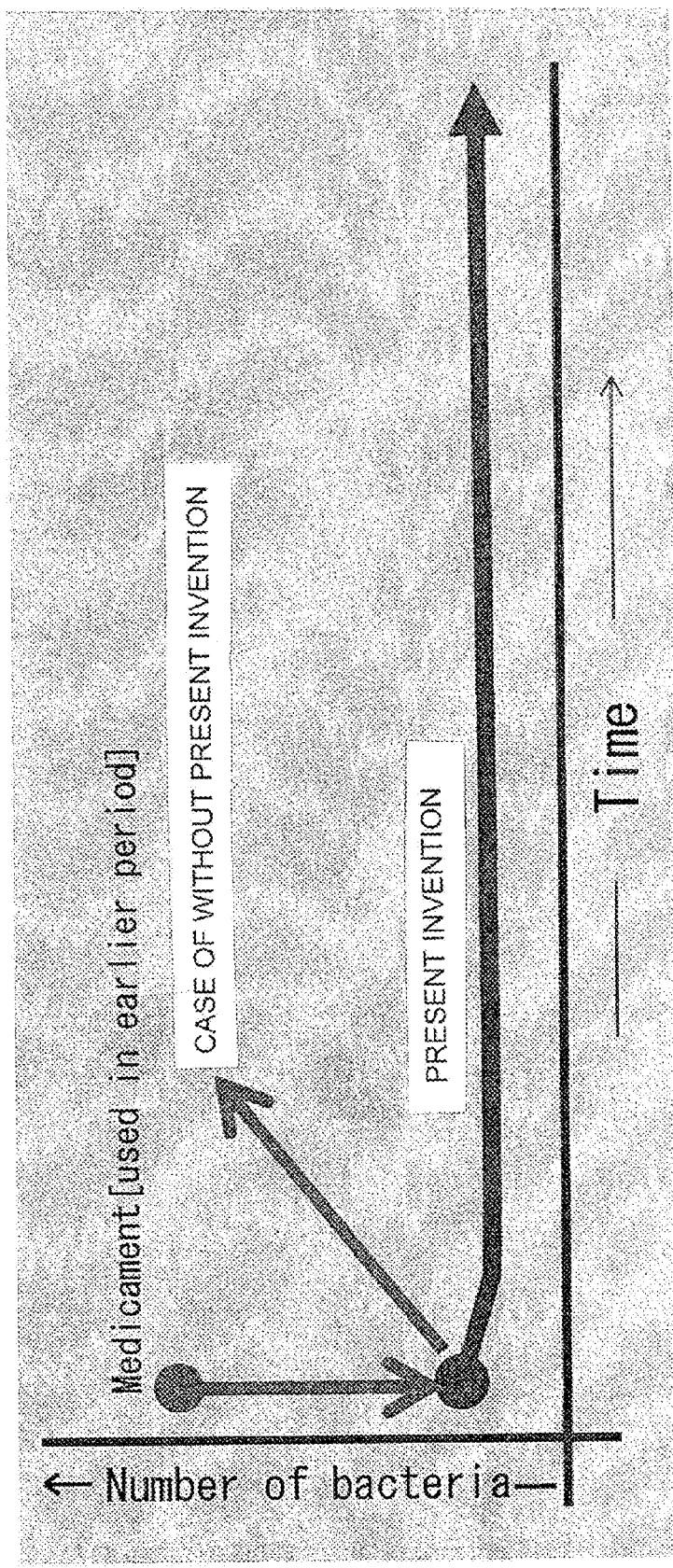
FIG. 11 is a graph showing one example of the efficiency and continuity of agents of the present invention.

And, in order to acquire further effect in wider fields, by using both of medicament that are existed and products or systems for that the agents of the present invention are used, it can be used as a new sterilizing system (sterilizing method) that contains prompt efficiency and continuity (see FIG. 11).

IMPLEMENTATION EXAMPLES AND COMPARISON EXAMPLES

Implementation Example 1

The following was prepared with the weight ratio of 100:10, particles with thermal bonding of $TiO_2$ powder (particle size 10 μm-50 μm) and silver powder (particle size 1 μm-50 μm).

Implementation Example 2

A stainless plate coated with the particles of Implementation Example 1 was prepared.

Comparison Example 1

The above Implementation Example 1, i.e. $TiO_2$ and silver particles that comprise thermal bonding were replaced with $TiO_2$ and silver particles without thermal bonding. Other conditions were exactly the same between Implementation Example 1 and Comparison Example 1.

Comparison Example 2

The above Implementation Example 1, i.e. $TiO_2$ and silver particles that comprise thermal bonding were replaced with solely $TiO_2$ particles without thermal bonding. Other conditions were exactly the same between Implementation Example 1 and Comparison Example 2.

Comparison Example 3

$TiO_2$ and silver, that were coated onto the stainless plate of the Implementation Example 2, that were thermal bonded too, were replaced with silver and zinc zeolite. Other conditions were exactly the same between Implementation Example 2 and Comparison Example 3.

0.02 g powder of the presently invented agent with Implementation Example 1 were mixed with 10 ml distilled water and 0.1 ml, 4.5×105 cfu/ml *Staphylococcus aureus* solution. 0.02 g powder of Comparison Example 1 were mixed with 10 ml distilled water and 0.1 ml, 4.5×105 cfu/ml *Staphylococcus aureus* solution. 0.02 g powder of Comparison Example 2 were mixed with 10 ml distilled water and 0.1 ml, 4.5×105 cfu/ml *Staphylococcus aureus* solution. After letting reactions occur for 0 minute and 240 minutes in the room temperature, the number of the *Staphylococcus aureus* was measured with agar plate culture method.

The results are as follows:

TABLE 1

|  | The number of bacteria after 0 hour (cfu/ml) | The number of bacteria after 4 hours (cfu/ml) | The decreasing rate after 4 hours (%) |
|---|---|---|---|
| Implementation Example 1 particles of $TiO_2$ and silver with thermal bonding | $1.3 \times 10^5$ | $1.3 \times 10^3$ | 99% |
| Comparison Example 1 particles of $TiO_2$ and silver without thermal bonding | $1.3 \times 10^5$ | $4.5 \times 10^4$ | 65% |
| Comparison Example 2 Solely particles of $TiO_2$ | $1.6 \times 10^5$ | $7.1 \times 10^4$ | 45% |

0.02 g powder of the presently invented agent with Implementation Example 1 was mixed with 0.1 ml, 4.5×10⁶ cfu/ml *Escherichia coli* solution. 0.02 g powder of Comparison Example 1 were mixed with 10 ml distilled water and 0.1 ml, 4.5×10⁶ cfu/ml *Escherichia coli* solution. 0.02 g powder of Comparison Example 2 were mixed with 10 ml distilled water and 0.1 ml, 4.5×10⁶ cfu/ml *Escherichia coli* solution. After letting reactions occur for 0 minute and 60 minutes in the room temperature, the number of *Escherichia coli* was measured with agar plate culture method.

The results are as follows:

TABLE 2

|  | The number of bacteria after 0 hour (cfu/ml) | The number of bacteria after 4 hours (cfu/ml) | The decreasing rate after 4 hours (%) |
|---|---|---|---|
| Implementation Example 1 particles of $TiO_2$ and silver with thermal bonding | $1.7 \times 10^6$ | $4.2 \times 10^3$ | 99% |
| Comparison Example 1 particles of $TiO_2$ and silver without thermal bonding | $1.7 \times 10^6$ | $2.6 \times 10^5$ | 85% |
| Comparison Example 2 solely particles of $TiO_2$ | $1.5 \times 10^6$ | $1.1 \times 10^6$ | 27% |

0.01 ml, 4.5×107 cfu/ml *Staphylococcus aureus* was inoculated onto the plate of Implementation Example 2. 0.01 ml, 4.5×107 cfu/ml *Staphylococcus aureus* was inoculated onto the plate of Comparison Example 3. Implementation Example 2: after letting reactions occur for 60 minutes, 180 minutes, Comparison Example 3: after letting reactions occur for 60 minutes, 240 minutes, the number of *Staphylococcus aureus* was measured with agar plate culture method.

Log 10 inactivation of test bacteria is as follows:

|  | Decreasing quantity after 1 hour | Decreasing quantity after 3 hours | Decreasing quantity after 4 hours |
|---|---|---|---|
| Implementation Example 2 | 3.02 | >5.9 | — |
| Comparison Example 3 | 3.65 | — | 4.64 |

Based on the above results, the agents of the present invention that comprise the thermal bonding of particles of $TiO_2$ and silver is considered to have good abilities to decompose organic matter.

In addition to the above, the present invention does not become a burden for the environment.

There are a variety of medical products used for the purpose of sterilizing bacteria, deactivating viruses, decomposing allergens, and deodorization. But such medical products have to do with the fact that the more effective they are the more intrinsically destructive they are to the human body and the natural world. However, the agents of the present invention do not influence the environment, since the agents do not dissolve into water and last for a long time and are effective for long periods of time.

It should be apparent that the above described embodiments are but a few which can be made by one of ordinary skill in the art without departing from the spirit and scope of the present invention.

The invention claimed is:

1. A sterilizing agent having a sterilizing effect without the presence of light manufactured by a means selected from the group consisting of (1) thermal bonding a metal (2) pressure bonding a metal and (3) thermal/pressure bonding a metal onto ceramic particles, wherein:
    the metal is silver and the ceramic is titanium dioxide;
    the crystal form of the titanium dioxide is anatase, rutile or mixtures thereof; and
    the sterilizing agent further includes adsorptive materials.

2. The sterilizing agent according to claim 1 wherein said metal is bonded ingrown into particles of the ceramic.

3. The sterilizing agent according to claim 1, wherein said adsorptive materials are Hydroxyapatite.

4. The sterilizing agent according to any one of claims 1, 2, and 3 wherein when the sterilizing agent is applied to *Staphylococcus aureus*, a decreasing Quantity of the *Staphylococcus aureus* after a predetermined time is larger than a decreasing quantity of the *Staphylococcus aureus* after the predetermined time when silver zinc zeolite is applied to the *Staphylococcus aureus*.

5. The method of making the sterilizing agent of (1) thermal bonding of claim 1 wherein said ceramic and said metal are bonded through a high temperature zone.

6. The method according to claim 5 wherein said high temperature zone is at about 2,900 degrees C.

7. The method of making the sterilizing agent of (2) pressure bonding of claim 1 wherein said ceramic and said metal are bonded through a ball mill.

8. The method according to claim 7 wherein said ball mill contains hard ball particles made from a material selected from the group consisting of alumina or zirconium and mixtures thereof.

9. The method of making the sterilizing agent using (3) thermal/pressure bonding of claim 1 wherein said ceramic and said metal are bonded with heat and pressure at the same time.

10. The method according to any one of claims 5, 7 and 9 wherein said ceramic and said metal particles are in a size range of 0.3 to 100 micrometers.

11. The method according to claim 10 wherein the particles of metal and ceramic are 0.3 to 50 micrometers.

12. The method according to claim 10 where the composition of the particles is 0.1% to 10% by weight silver and 90% to 99.9% by weight titanium dioxide.

13. A slurry sterilizing dispersing element comprising the sterilizing agent of any one of claims 1, 2 and 3 mixed with a liquid solution.

14. The slurry sterilizing dispersing element according to claim 13 wherein the liquid solution can be used safely on the human body and/or other surfaces.

15. A sterilizing means comprising the sterilizing agent of any one of claims 1, 2 and 3 provided in the fibres of a woven or non-woven fabric or paper, wood, plastics, metals, ceramics, compound products, paints, resin films, water, cleaning solutions, air filters and printing ink.

16. A method for sterilizing surfaces comprising the steps of applying the paint of any one of claims 1, 2 and 3 to housing materials for indoor use, furniture surface.

17. A method for giving fabric a sterilizing effect comprising the steps of impregnating any one of claims 1, 2 and 3 into the fibres of a woven or non-woven fabric.

18. A method for giving fabric a sterilizing effect comprising the steps of printing any one of claims 1, 2 and 3 to a surface of fibres of a woven or non-woven fabric.

19. A method for sterilizing surfaces comprising applying the resin film of any one of claims 1, 2 and 3 to housing materials for indoor use, furniture surface.

20. A sterilizing linen comprising the sterilizing agent of any one of claims 1, 2 and 3 provided in any one of cloth sheets, cloth pillow cases, towels, wash clothes and curtains.

21. Materials comprising the sterilizing agent of any one of claims 1, 2 and 3.

22. Products comprising the sterilizing agent of any one of claims 1, 2 and 3.

23. The materials of claim 21 provided in any one of adhesive bandage, ointment, gauze, catheter, and endoscope.

24. The materials of claim 21 provided in any one of drinking water, rain water, hot spring and cooling tower.

25. The materials of claim 21 provided in any one of hydroponics, aquaculture, soil amendment, washing and cleaning of vegetables, preservation for foodstuff, and antisepsis for foodstuff.

26. The materials of claim 21 provided in any one of wallpaper, ceiling material, and flooring.

27. The sterilizing agent according to claim 1 wherein the sterilizing agent is provided in any one of fibres of a woven or non-woven fabric or paper, wood, plastics, metals, ceramics, compound products, paints, resin films, water, cleaning solutions, air filters and printing ink.

28. A sterilizing agent according to claim 1, wherein the silver is bonded onto the titanium dioxide with thermal bonding, and
    when the sterilizing agent is applied to *Staphylococcus aureus* or *Escherichia coli*, a decreasing rate (%) of the *Staphylococcus aureus* or *Escherichia coli* after a predetermined time is larger than a decreasing rate (%) of the *Staphylococcus aureus* or *Escherichia coli* after the predetermined time when titanium dioxide and silver without thermal bonding or solely titanium dioxide is applied to the *Staphylococcus aureus* or *Escherichia coli*.

* * * * *